United States Patent
Siess et al.

(10) Patent No.: US 11,759,622 B2
(45) Date of Patent: *Sep. 19, 2023

(54) BLOOD PUMP

(71) Applicant: Abiomed Europe GmbH, Aachen (DE)

(72) Inventors: Thorsten Siess, Aachen (DE); Christof Malzkorn, Aachen (DE); Martin Kortyka, Aachen (DE); Christian Moser, Aachen (DE)

(73) Assignee: ABIOMED EUROPE GMBH, Aachen (DE)

( * ) Notice: Subject to any disclaimer, the term of this patent is extended or adjusted under 35 U.S.C. 154(b) by 26 days.

This patent is subject to a terminal disclaimer.

(21) Appl. No.: 17/520,407

(22) Filed: Nov. 5, 2021

(65) Prior Publication Data

US 2022/0168556 A1 Jun. 2, 2022

Related U.S. Application Data

(63) Continuation of application No. 16/484,423, filed as application No. PCT/EP2018/052797 on Feb. 5, 2018, now Pat. No. 11,191,945.

(30) Foreign Application Priority Data

Feb. 7, 2017 (EP) ..................... 17155078

(51) Int. Cl.
*A61M 60/419* (2021.01)
*A61M 60/216* (2021.01)
(Continued)

(52) U.S. Cl.
CPC .......... *A61M 60/419* (2021.01); *A61M 60/13* (2021.01); *A61M 60/216* (2021.01);
(Continued)

(58) Field of Classification Search
None
See application file for complete search history.

(56) References Cited

U.S. PATENT DOCUMENTS

| | | | |
|---|---|---|---|
| 5,491,622 A * | 2/1996 | Carosa | H02M 7/48 363/56.02 |
| 5,911,685 A | 6/1999 | Siess et al. | |

(Continued)

FOREIGN PATENT DOCUMENTS

| | | |
|---|---|---|
| EP | 0989656 A1 | 3/2000 |
| JP | H0666901 A | 3/1994 |

(Continued)

OTHER PUBLICATIONS

International Search Report and Written Opinion for International Application No. PCT/EP2018/052797 dated Apr. 5, 2018 (8 pages).

(Continued)

*Primary Examiner* — Paula J Stice
(74) *Attorney, Agent, or Firm* — Botos Churchill IP Law LLP

(57) ABSTRACT

Blood pump for percutaneous insertion into a heart's ventricle comprising an electrical motor for driving the blood pump, the electrical motor comprising at least tree motor winding units, wherein each motor winding unit is individually connectable to a power supply via two separate phase supply lines connected to the respective motor winding unit terminals. Motor controller for driving and controlling the electrical motor of the blood pump, wherein the motor controller comprises corresponding phase supply line driving units for each motor winding units of the electrical motor of the blood pump which phase supply line driving units are connected via the corresponding two-phase supply lines with the corresponding motor winding unit. Blood pump system comprising the blood pump and the motor controller. Control method for controlling the power supply to the (Continued)

motor winding units of the blood pump, wherein the method comprises: detecting a fault of one of the motor winding units, and in case of a detected faulty motor winding unit, switching off the corresponding phase supply line driving unit of the faulty motor winding unit and further operating the electrical motor by the remaining motor winding units, or, alternatively, adjusting driving parameters of the faulty motor winding unit and further operating the electrical motor by all motor winding units. Use of at least three independent motor winding units in an electrical motor for driving of a blood pump for percutaneous insertion, which motor winding units are individually connected to corresponding power supply via corresponding two separate phase supply lines connected to respective motor winding unit terminals of one of the at least three motor winding units.

10 Claims, 3 Drawing Sheets

(51) Int. Cl.
 *A61M 60/538* (2021.01)
 *A61M 60/422* (2021.01)
 *A61M 60/13* (2021.01)
(52) U.S. Cl.
 CPC ........ *A61M 60/422* (2021.01); *A61M 60/538* (2021.01); *A61M 2205/3365* (2013.01)

(56) References Cited

U.S. PATENT DOCUMENTS

| | | | |
|---|---|---|---|
| 5,964,694 A | * | 10/1999 | Siess .................. A61M 60/416 623/3.1 |
| 6,278,251 B1 | | 8/2001 | Schoeb |
| 8,864,643 B2 | * | 10/2014 | Reichenbach .......... F04D 17/08 600/16 |
| 9,545,468 B2 | | 1/2017 | Aboul-Hosn et al. |

FOREIGN PATENT DOCUMENTS

| | | |
|---|---|---|
| JP | 2000511455 | 9/2000 |
| JP | 2000511455 A | 9/2000 |
| JP | 2016189647 A | 11/2016 |
| WO | 2012059368 A2 | 5/2012 |

OTHER PUBLICATIONS

Office Action from corresponding Indian Application No. 202238033796 dated Sep. 26, 2022 (8pp.).

Office Action from corresponding Japanese Application No. 2019-542475 dated Oct. 25, 2022 (10 pp.).

Office Action from corresponding Korean Patent Application No. 10-2019-7024391 dated Jan. 20, 2023 (13 pages).

Office Action issued in corresponding Chinese Patent Application No. 201880008332.0 dated Sep. 2, 2021, (25 pp).

Office Action issued in corresponding Japanese Patent Application No. 2019-542475 dated Mar. 15, 2022 (9 pp.).

* cited by examiner

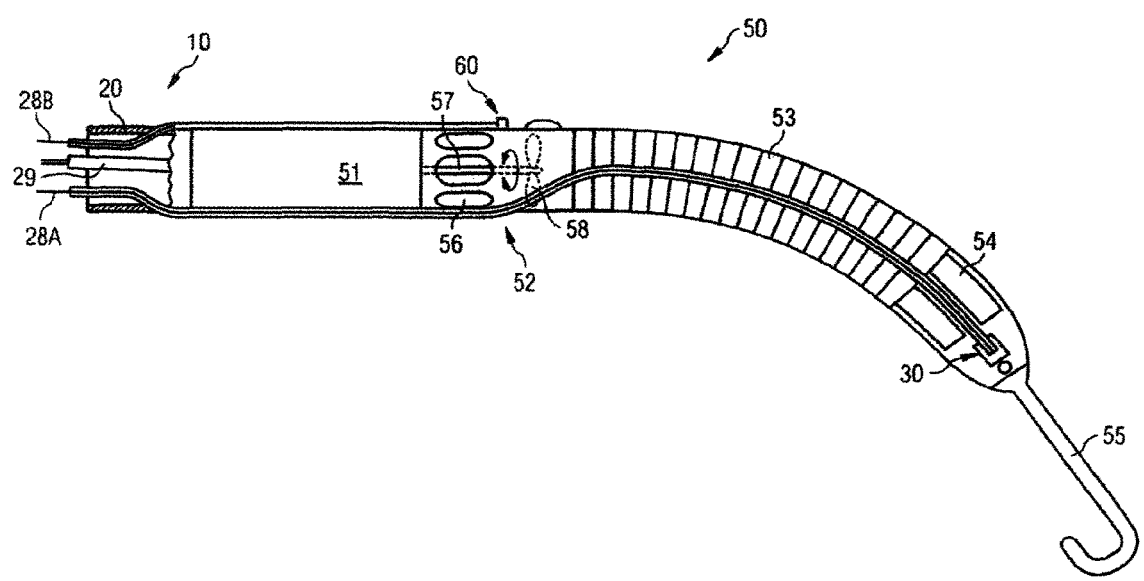
Fig. 1
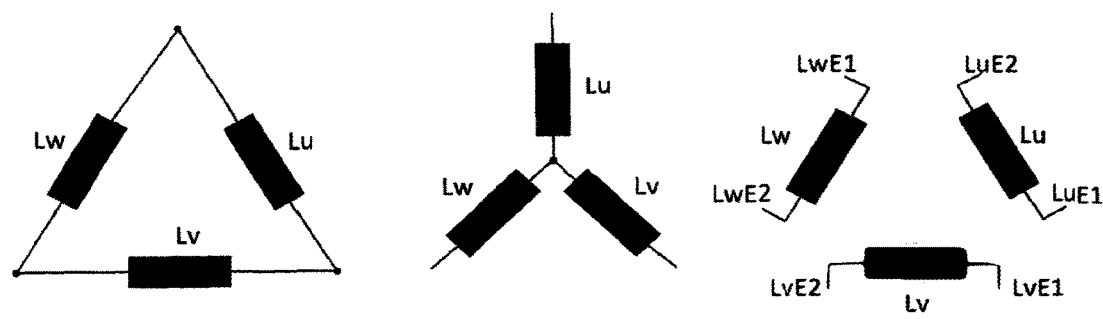
Fig. 2 (a) (b) (c)

BLOOD PUMP

CROSS-REFERENCE TO RELATED APPLICATIONS

The present application is a continuation of U.S. patent application Ser. No. 16/484,423, filed on Aug. 7, 2019, now U.S. Pat. No. 11,191,945, which is a national phase entry under 35 U.S.C. § 371 of International Application No. PCT/EP2018/052797, filed Feb. 5, 2018, published as International Publication No. WO 2018/146045 A1, which claims priority to European Patent Application No. 17155078.3, filed Feb. 7, 2017, the disclosures of which are hereby incorporated herein by reference.

FIELD OF THE INVENTION

The present invention concerns the field of ventricular assist devices (VAD) for percutaneous insertion. In particular, the invention relates to the circuitry configuration of motor winding units in the motor of the VAD, such as percutaneous insertable blood pump, for example an intravascular rotary blood pump and the control as well as control device of such a VAD.

BACKGROUND OF THE INVENTION

VADs driven by an electrical motor having motor windings are in general known. One particular example of a VAD such as a percutaneous insertable blood pump is a catheter-based rotary blood pump arranged to be placed or implanted directly through blood vessels into the heart for several hours or days for assisting the heart function until recovery.

U.S. Pat. No. 5,911,685 A discloses an exemplary intravascular rotary blood pump. However, there are other types of VADs comprising electrical motors as well.

An electrical motor for driving the VAD is one important component of the VAD with regard to functionality of the VAD and so for providing the required assistance to the heart of a patient. Failure of the motor may cause serious problems and even if the VAD can be replaced such a replacement imposes an unnecessary risk.

SUMMARY OF THE INVENTION

It is a first object of the present invention to provide an improved electrical drive for VADs by which the risk of a failing electrical motor can be reduced and in particular a complete drop out of the electrical motor can be avoided.

Further, it is a second object of the present invention to provide an improved control method and device for an improved electrical motor achieving the first object, for further operating the electrical motor in the event of a failing motor winding.

At least one of the objects is achieved by the features of the respective independent claims. Further embodiments are defined in the respective dependent claims.

The core idea of the present invention is to use an electrical motor for driving the VAD, in particular a percutaneous insertable blood pump such as an intravascular rotary blood pump, in which the motor windings are arranged in a circuitry configuration that avoids any circuitry interconnection between anyone and the respective other motor windings. Preferably, all motor windings are individually operated via separate supply lines. Advantageously, the electrical motor may still be operated if there is failure with anyone of the motor windings by placing the affected motor winding out of operation or operating the affected motor winding with adjusted parameters. For example, if there is an interruption in one of the phase supply lines for any one of the motor windings, the electrical motor can still be operated by means of the remaining motor windings. For example, if there is a short circuit between two particular windings, one of the affected windings can be placed out of operation so that the electrical motor can still be operated by means of the remaining motor windings. For example, if there is a short circuit within one particular winding (e.g., a turn-to-turn short circuit), the affected winding can be placed out of operation or operated with adjusted parameters so that the electrical motor can still be operated by means of the remaining motor windings. For example, if there is a fault current from a particular winding to, for example, the pump's casing, the affected winding can be placed out of operation so that the electrical motor can still be operated by means of the remaining motor windings.

A first aspect of the invention provides a blood pump for percutaneous insertion such as e.g., intravascular application. The blood pump comprises an electrical motor for driving the blood pump. The electrical motor comprises at least tree motor winding units. Each motor winding unit is arranged and configured to be individually connected to a power supply through two corresponding separate phase supply lines one of which is connected to one of two motor winding unit terminals and the other is connected to the other one of the motor winding terminals.

A particular motor winding unit includes at least one corresponding motor winding, but is not limited to only one particular winding. That is to say, a motor winding unit may include more than one winding. In particular, a motor winding unit may include more than one motor winding which are connected in parallel to each other. For example, a motor winding unit may include multilayer windings in which more than one winding are implemented in different layers and are connected in parallel forming the motor winding unit. For example, one winding may consist of two parallel connected wirings disposed in different layers and connected in parallel forming the respective motor winding unit.

Preferably, the electrical motor is a synchronous motor. Most preferably, the motor is a permanent magnet excited synchronous motor, i.e., comprises a rotor including a permanent magnet.

Preferably, the electrical motor comprises at least three motor winding units and for each motor winding unit two corresponding phase supply lines. In a particular embodiment the electrical motor comprises three motor winding units, wherein each of the corresponding motor winding unit terminals is connected to one corresponding phase supply line.

A second aspect of the invention provides a motor controller for driving and controlling the electrical motor of a blood pump according to the first aspect of the present invention. The motor controller comprises corresponding switchable phase supply line driving units for each motor winding unit. Each switchable phase supply line driving unit is connected via corresponding two-phase supply lines with one of the motor winding units.

Preferably, the phase supply line driving units are implemented by two half bridge units which are switchable for a cooperative control of the electrical power supplied to each of the motor winding units.

Preferably, the motor controller comprises at least one of: respective phase current measuring units for measuring the actual value of the electrical current through the corresponding motor winding unit; a total current measuring unit for measuring the actual value of the total electrical current through all motor winding units; and respective measuring units configured for measuring a respective induced back electromagnetic force, back EMF, voltage also called counter electromagnetic force, CEMF, voltage for each motor winding units at the moment when the respective motor winding unit is not driven, i.e. the respective motor winding unit is disconnected from the power supply.

Preferably, the motor controller comprises a control unit operatively connected to and for controlling the phase supply line driving units and configured to drive and control at least one of the rotational speed of the electrical motor, the rotational direction of the electrical motor, and the torque produced by the electrical motor.

Preferably, the control unit is configured to detect a fault in one of the motor winding units. Further, the control unit is configured, in case of a detected faulty motor winding unit, to switch off the corresponding phase supply line driving unit of the faulty motor winding unit and to further operate the electrical motor by the remaining motor windings. Alternatively, the control unit may be configured to further drive the faulty motor winding unit with adjusted parameters and to further operate the electrical motor by all motor windings. That is to say, the blood pump can be kept in operation by means of the remaining motor winding units alone or by means of all motor winding units wherein the faulty motor winding unit is operated with adjusted driving parameters.

Preferably, a motor winding unit is determined being faulty in case of at least one of:

(a) an interruption in the wire of the motor winding unit or in at least one of the corresponding phase supply lines of the motor winding unit;

(b) a current leakage of the motor winding unit to a casing of the electrical motor;

(c) a short circuit between wire turns of the motor winding unit.

Preferably, the control unit is configured to detect the faulty motor winding unit, i.e., one of the afore-mentioned faults (a) to (c) based on at least one of: the respective actual electrical current through the motor winding unit or motor winding units and a comparison of the actual electrical voltage of the motor winding unit or motor winding units.

Alternatively, a fault in a motor winding unit may comprise a short circuit between the wires of two of the motor winding units, i.e., resulting in the two motor winding units being faulty. Preferably, the control unit is configured to detect the two faulty motor winding units based on a comparison of the actual electrical current through the two faulty motor winding units. Preferably, in case of such two faulty winding units, the control unit is configured to determine one of the two faulty motor winding units as the faulty motor winding unit the corresponding phase supply line driving unit is to be switched off or to be operated with adjusted parameters.

A third aspect of the invention provides a blood pump system comprising a blood pump according to the first aspect of the present invention and a motor controller according to the second aspect of the present invention.

A fourth aspect of the invention provides a control method for controlling the power supply to motor winding units of a blood pump, preferably according to the first aspect of the present invention. The method comprises: (i) detecting a fault in one of the motor winding units; (ii) in case of a detected faulty motor winding unit: in a first alternative, switching off a corresponding phase supply line driving unit driving the faulty motor winding unit and further operating the electrical motor by controlling the phase supply line driving units of the remaining motor windings; in a second alternative, adjusting driving parameters of the faulty motor winding unit and further operating the electrical motor by controlling the phase supply line driving units of all motor windings.

Preferably, the step of detecting a fault in one of the motor winding units comprises but is not limited to detecting at least one of:

(a) an interruption in the wire of the faulty motor winding unit or in the corresponding phase supply lines of the faulty motor winding unit;

(b) a current leakage of the faulty motor winding unit to a casing of the electrical motor;

(c) a short circuit between wire turns of the faulty motor winding unit; and (d) a short circuit between the wires of two of the motor winding units.

Preferably, the step of detecting a fault in one of the motor winding units is based on at least one of the respective actual electrical current through the motor winding units, a comparison of the actual electrical voltage drop at the motor winding units, and a comparison of the actual electrical current through the faulty motor winding units.

A fifth aspect of the invention concerns the use of at least three independent motor winding units in an electrical motor for driving of a blood pump for percutaneous insertion. Each motor winding unit is arranged and configured to be individually connected to a power supply via corresponding two separate phase supply lines which are connected to a respective one of two motor winding unit terminals of the corresponding motor winding unit.

Finally, with regard to the blood pump of the first aspect of the present invention, the motor controller of the second aspect of the present invention, the blood pump system of the third aspect of the present invention, the control method of the fourth aspect of the present invention, or the use of the fifth aspect of the present invention, in any case, the electrical motor is preferably an integral component to the blood pump. Since the blood pump is configured for being completely inserted percutaneously into a patient's body, the electrical motor as integral part of the blood pump is inserted as well, when the blood pump is inserted into a patient. In turn, the motor controller for providing electrical power to and controlling of the electrical motor is preferably located outside the patient's body. Just a connection for power supply to and control of the operation of the electrical motor is to be passed through a catheter form outside a patient percutaneously into the body of the patient to the blood pump and correspondingly to the electrical motor.

DETAILED DESCRIPTION OF THE DRAWINGS

Hereinafter the invention will be explained by way of examples with reference to the accompanying drawings; in which FIG. 1 shows an example for a VAD for percutaneous insertion driven by an electrical motor.

FIG. 2 shows circuitry configurations for three motor winding units, namely (a) the delta configuration, (b) the star or wye configuration, and (c) configuration with open wiring ends.

DETAILED DESCRIPTION

Figure 3:
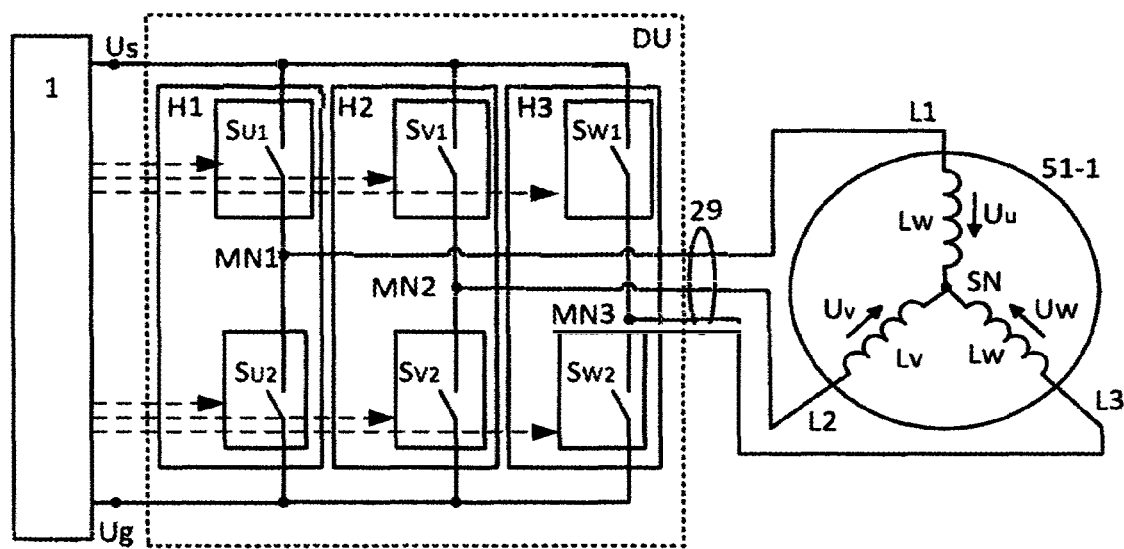
FIG. 3 illustrates principle of driving an electrical motor with three motor winding units in star configuration by pulse with modulated control of corresponding switches between a power supply and the three power supply lines of the motor winding units.

FIG. 1 shows an example for a VAD for percutaneous insertion driven by an electrical motor comprising corresponding motor winding units. The VAD is a micro axial rotary blood pump 50, in particular a catheter-based micro axial rotational blood pump for percutaneous insertion through a patient's vessel into a patient's heart (in the following for short called "blood pump 50"). Such a blood pump is, for example, known from U.S. Pat. No. 5,911,685 A.

The blood pump 50 is based on a catheter 10 by means of which the blood pump 50 can be temporarily introduced via a vessel into a ventricle of a patient's heart. The blood pump 50 comprises in addition to the catheter 10 a pumping device fastened to the end of a catheter tube 20. The rotary pumping device comprises an electrical motor 51 and a pump section 52 located at an axial distance therefrom. A flow cannula 53 is connected to the pump section 52 at its one end, extends from the pump section 52 and has an inflow cage 54 located at its other end. The inflow cage 54 has attached thereto a soft and flexible tip 55. The pump section 52 comprises a pump housing with outlet openings 56. Further, the pumping device comprises a drive shaft 57 protruding from the electrical motor 51 into the pump housing of the pump section 52. The drive shaft 57 drives an impeller 58 as a thrust element. During operation of the blood pump 50, blood can be sucked through the inflow cage 54 and discharged through the outlet openings 56 by means of the rotating impeller 58 driven by an electrical motor 50 via the drive shaft 57.

Through the catheter tube 20 of the catheter 10 pass three lines, namely two signal lines 28A, 28B and a power supply line 29 for suppling electrical power to the electrical motor 51 of the pumping device. The signal lines 28A, 28B and the power-supply line 29 are attached at their proximal end to a control device (not shown) for control of the pumping device. The signal lines 28A, 28B are parts of blood pressure sensors with corresponding sensor heads 30 and 60, respectively. The power supply line 29 comprises separate phase supply lines for supplying electrical power to each motor winding unit of the electrical motor 51 of the motor section. The electrical motor 51 is preferably a synchronous motor. In an exemplary configuration the electrical motor comprises three motor winding units for driving a rotor (not shown) coupled with the drive shaft 57. The rotor may comprise at least one field winding. Alternatively, the rotor comprises a permanent magnet resulting in a permanent magnet excited synchronous motor. In a particular embodiment, a particular motor winding unit includes two parallel connected windings which are disposed in different layers and connected in parallel.

The blood pump 50 is a micro axial rotary blood pump, wherein "micro" indicates that the size is small enough so that the blood pump can be percutaneously inserted into a heart's ventricle via blood vessels leading to the ventricle. This also defines the blood pump 50 as an "intravascular" blood pump for percutaneous insertion. "Axial" indicates that the arrangement of the electrical motor 51 for driving the pump section 52 are arranged in an axial configuration. "Rotational" means that the pump functionality is based on the rotating operation of the trust element, e.g., the impeller, driven be the rotational electrical motor 51.

Preferably and as shown in FIG. 1, the electrical motor 51 is one component of the blood pump 50 which is configured to be completely inserted percutaneously into a patient's body. Usually, the blood pump 50 is inserted into a patient's body via vessels, for example leading to a ventricle of the patient's heart. As discussed above, the blood pump 50 is based on the catheter 10 by which the insertion of the blood pump 50 through the vessels can be performed and through which the power supply line 29 can be passed for supplying electrical power to and control of the electrical motor 51. That is to say, a motor controller (e.g., 100 in FIG. 4) providing electrical power to and controlling of the electrical motor 51 is located outside the patient's body. Thus, only the connection (e.g., 29) for power supply to and control of the operation of the motor 51 run through the catheter 10. This is totally different to blood pumps, which are driven via a rotating driving wire laid through a catheter so that just the pump section is to be inserted into a patient's body whilst the driving electrical motor can be located outside the patient's body. In this case, a failing electrical motor may be replaced more easily.

FIG. 2 shows respective circuitry configurations for the electrical motor 51 of the blood pump 50 in FIG. 1. By way of example, the electrical motor comprises three motor winding units Lu, Lv, Lw. In FIG. 2(a) the motor winding units Lu, Lv, Lw are connected in the delta circuit configuration. In FIG. 2(b) the motor winding units Lu, Lv, Lw are connected in the star or wye circuit configuration.

FIG. 2(c) shows the motor winding units Lu, Lv, Lw in a configuration with open wiring ends, commonly called "open end windings" configuration. The shown configuration is characterized by the fact that there is no intended circuit interconnection between anyone of the three motor winding units Lu, Lv, Lw to the other two motor winding units. In this configuration, anyone of the tree motor winding units Lu, Lv, Lw can be supplied with electrical power independently from the other motor winding units.

It is worth to be noted, a particular motor winding unit includes at least one particular motor winding, but is not limited to one winding. A motor winding unit may include more than one motor winding. In particular, a motor winding unit may include more than one motor winding which are connected in parallel to form the motor winding unit. For example, one motor winding unit may consist of two parallel connected wirings. The different windings may be disposed in different layers and may be connected in parallel at their respective wiring ends forming the terminals of the motor winding unit.

FIG. 3 illustrates the conventional driving of the electrical motor 51-1 having three motor winding units Lu, Lv, Lw in the configuration of FIG. 2(b) by means of a pulse with modulated control of corresponding switches Su1 and Su2, Sv1 and Sv2, Sw1 and Sw2 respectively connected to one of two power supply nodes Us, Ug and respectively to only one of three power supply lines L1, L2, L3 supplying one corresponding motor winding unit Lu, Lv, Lw.

The electrical motor 51-1 comprises the motor winding configuration as used in the micro axial rotary blood pump known from U.S. Pat. No. 5,911,685 A. The three motor winding units Lu, Lv, Lw are connected together with one of their terminals at a star node SN while the respective other terminal of each motor winding unit are connected through one of corresponding power supply lines L1, L2, L3 to corresponding middle nodes MN1, MN2, MN3 of respective three half bridges H1, H2, H3 respectively comprising two semiconductor switches, e.g., power MOSFETs, illustrated as the switches Su1 and Su2, Sv1 and Sv2, Sw1 and Sw2. Each of the three half bridges H1, H2, H3 defines a respective phase supply line driving unit which is controlled by control unit 1. The three half bridges H1, H2, H3, i.e., phase supply line driving units, may be integrated in or implemented by one driving unit DU.

Each of the half bridges H1, H2, H3 is controlled by control unit 1 configured to control the respective switches Su1 and Su2, Sv1 and Sv2, Sw1 and Sw2 by means of pulse width modulation such that the waveform of the voltages driving the particular motor winding units Lu, Lv, Lw have a 120.degree. phase difference with respect to anyone of the waveforms of the respective voltages driving the other two motor windings.

The half bridges H1, H2, H3 are respectively connected to the control unit 1 which also provides the supply voltage Us and a reference voltage Ug, e.g., ground. The respective control of the switches in one half bridge H1, H2, H3 is indicated in FIG. 3 by corresponding arrows from the control unit 1 to the respective switches Su1 and Su2, Sv1 and Sv2, Sw1 and Sw2. By switching the respective half bridges H1, H2, H3, the respective electrical current supplied to the corresponding motor winding unit Lu, Lv, Lw is switched resulting in a corresponding change of the magnetic field produced by the particular motor winding unit. Thereby, the motor winding units produce a rotating magnetic field for moving a rotor (not shown) of the motor 51-1. The rotor comprising an excited field winding is correspondingly forced to rotate.

The corresponding control of the switches Su1 and Su2, Sv1 and Sv2, Sw1 and Sw2 in the half bridges H1, H2, H3 (phase supply line driving units) allows for control of the rotational direction and rotational velocity of the electrical motor 51-1 as well as for the torque produced by the electrical motor 51-1. For example, in the known blood pump 50 shown in FIG. 1 the synchronous motor 51 with three motor winding units Lu, Lv, Lw is operated in star configuration. Accordingly, the supply line 29 shown in FIG. 1 running through the catheter tube 20 comprises three phase supply lines L1, L2, and L3 for supplying electrical power to the respective motor winding unit.

Figure 4:
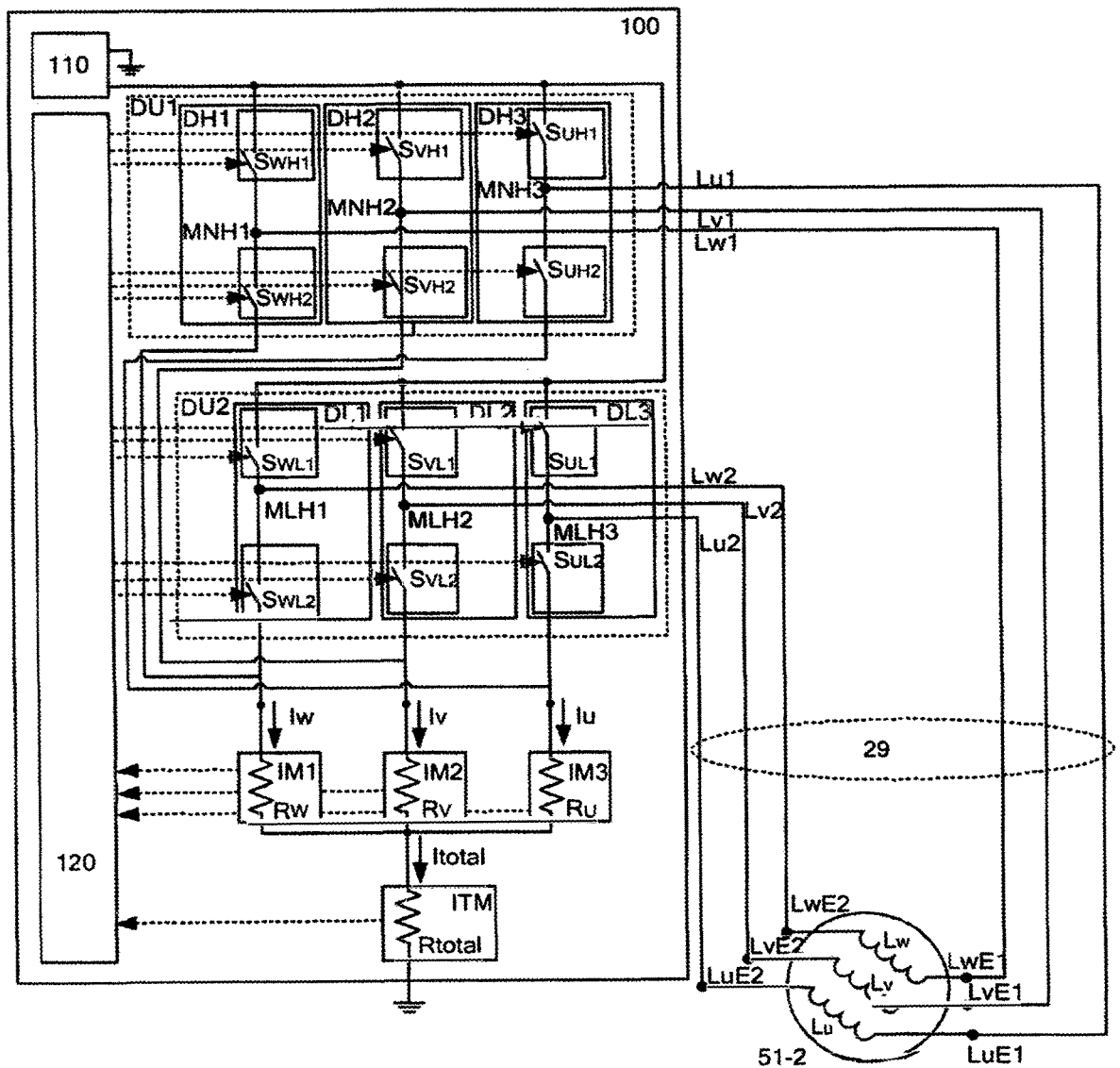
FIG. 4 shows one particular embodiment of the herein proposed new configuration of the motor winding units in the electrical motor of a blood pump for percutaneous insertion, and further illustrates by means of a simplified schematic circuitry diagram the basic configuration of the driving stage for the electrical motor.

FIG. 4 shows one particular embodiment of the herein proposed new configuration of the motor winding units in the electrical motor 51-2 of a blood pump for percutaneous insertion such as the one shown in FIG. 1. Further, FIG. 4 illustrates by means of a simplified schematic circuitry diagram the basic configuration of a driving stage for the electrical motor 51-2.

As mentioned before and as illustrated by FIG. 1, the electrical motor 51-2 is one integral component of the blood pump 50. Thus, with the blood pump 50, also the electrical motor 51-2 is completely inserted percutaneously into a patient's body. Also as discussed above, the blood pump 50 is based on the catheter 10 by which the insertion of the blood pump 50 through the vessels is performed and through which the power supply line 29 is guided for supplying electrical power to and control of the electrical motor 51-2. The power supply line 29 includes six individual separate phase supply lines Lw1, Lv1, and Lu1, Lw2, Lv2, and Lu2 (to be discussed in more detail below). A motor controller 100 amongst others providing electrical power to and controlling the electrical motor 51-2 will be located outside the patient's body. In other words, the connection for power supply to and control of the operation of the motor 51-2 pass through the catheter 10.

The electrical motor 51-2 comprises the three motor winding units Lu, Lv, Lw. It is noted that there may be used more than three motor winding units as well. Each motor winding unit Lu, Lv, Lw is individually connected at both respective motor winding unit terminals LwE1 and LwE2, LvE1 and LvE2, and LuE1 and LuE2 with one individual separate phase supply line Lw1, Lv1, and Lu1, Lw2, Lv2, and Lu2. Each of the two-phase supply lines of one particular motor winding unit Lu, Lv, Lw is connected to one corresponding half bridge circuit DH1, DH2, DH3, DL1, DL2, DL3. Each half bridge circuit DH1, DH2, DH3, DL1, DL2, DL3 is comprised of two corresponding semiconductor switches SwH1 and SwH2, SvH1 and SvH2, SuH1 and SuH2, SwL1 and SwL2, SvL1 and SvL2, SuL1 and SuL2, as described in connection with FIG. 3.

For instance, with respect to the motor winding unit Lw, a first winding unit terminal LwE1 is connected via a first phase supply line Lw1 to a middle node MNH1 of the half bridge circuit DH1, while the second winding end LwE2 is connected via a second phase supply line Lw2 to the middle node MNL1 of the corresponding second half bridge circuit DL1. Each of the two half bridge circuits DH1, DL1 comprises two respective semiconductor switches SwH1 and SwH2, SwL1 and SwL2. The two half bridge circuits DH1, DL1 together define the phase supply line driving unit for the motor winding unit Lw. The same applies correspondingly for the other half bridges and motor winding units.

In comparison to the configuration shown in FIG. 3, the electrical motor 51-2 in FIG. 4 is driven and controlled by a motor controller 100 comprising in principle two driving units DU1, DU2. Each of the two driving units DU1, DU2 is respectively connected to respective first winding unit terminals of the motor winding units Lu, Lv, Lw. In a particular implementation, for example, the driving units DU1, DU2 may be implemented by an integrated circuit (IC), such as a DRV8312 three phase pulse width modulation driving unit from Texas Instruments.

For measuring the actual electrical current Iv, Iu, Iw passing through one particular motor winding unit Lw, Lv, Lu, the driving units DU1, DU2 are connected to respective current measuring units IM1, IM2, IM3 which in principle are connected in series with the corresponding motor winding unit Lw, Lv, Lu. For example, the actual electrical current passing through one particular motor winding unit Lw, Lv, Lu can be determined as corresponding to the electrical voltage drop over a current sensing element, such as a shunt resistor. In the embodiment shown in FIG. 4, the current sensing units IM1, IM2, IM3 are implemented by corresponding shunt resistors Rw, Rv, Ru.

In a corresponding manner, the motor controller 100 comprises a measuring unit ITM for the total electrical current passing through all motor winding units Lw, Lv, Lu. The total current measuring unit ITM comprises a current sensing element and is connected in series with a common node of all phase supply lines, which in principle are connected as the motor winding units itself in parallel to each other. The current sensing unit ITM for the total electrical current is implemented by a shunt resistor Rtotal, the voltage drop thereof can be measured and is proportional to the total electrical current Itotal.

Further, the control unit 120 comprises sensing inputs for receiving the measurement values for the actual electrical currents Iv, Iu, Iw for each individual motor winding unit Lw, Lv, Lu as well as for the total electrical current Itotal passing through all motor winding units Lw, Lv, Lu. Further the control unit 120 is operatively connected to the power supply unit 110 for receiving the actual voltage supplied via the driving units DU1, DU2.

Furthermore, a corresponding voltage measurement is also implemented at the respective middle nodes MNH1, MNH2, and MNH3 in driving unit DU1 and/or MNL1, MNK2, MNL3 in driving unit DU2 for measuring the induced counter electromagnetic force, CEMF, voltages at each motor winding unit when the respective motor winding unit is currently not driven, i.e., any one of the switches in the corresponding half bridges is open.

Further, output control lines run from the control unit 120 to the respective semiconductor switches of the half bridges DH1, DH2, DH3, DL1, DL2, DL3 for control thereof.

It is noted the current sensing lines and the control lines are only shown schematically in FIG. 4 to keep the Figure simple; by way of example, there is an arrow from the current measuring unit IM1 with shunt resistor Rw to the control unit 120 representing the input of a measuring value for the actual electrical current lw in the motor winding Lw to the control unit 120. Similarly, an arrow from the control unit 120 to the semiconductor switch SwL2 of the half bridge DL1 in the driving unit DU2 illustrates that the operation of the switch SwL2 is under control of the control unit 120 as are the other switches.

In principle the control of the rotational direction, rotational speed and the produced motor torque of the electrical motor 51-2 is similar to that in the configuration shown in FIG. 3. However, the herein proposed configuration provides some particular advantages.

Firstly, the control unit 120 is configured to detect faults in anyone of the motor winding units Lu, Lv, Lw. Based on a detected faulty motor winding unit, the control unit 120 is configured to switch off the corresponding half bridges DH1, DH2, DH3, DL1, DL2, DL3 connected to the faulty motor winding unit, once the particular motor winding unit was detected as faulty. Due to the individual control of each of the motor winding units Lu, Lv, Lw, the electrical motor 51-2 can be further controlled and operated, alternatively by means of the remaining motor winding units only, particularly by control of the corresponding remaining half bridges, or by means of all motor winding units, wherein the driving parameters for the faulty motor winding unit are adjusted.

Advantageously, a faulty motor winding unit may be defined at least by detecting one of the following circuitry faults.

For example, there may be an interruption in the wire of the motor winding unit or in the corresponding phase supply lines of a motor winding unit, which corresponds to a fault in the particular motor winding unit.

For example, due to an insulation failure in one of the motor winding units there may be a current leakage between the motor winding and the casing of the electrical motor 51-2.

For example, there may be a short circuit between wire turns of a particular motor winding unit resulting in a reduced inductance of the corresponding motor winding unit, also defining a faulty motor winding unit.

In all these forgoing fault cases, the control unit 120 is configured to detect the respective faulty motor winding unit based on the respectively measured actual electrical current through the motor winding units and/or a comparison of the actual electrical voltage drop at the motor winding units.

Moreover, for example, a fault in a motor winding unit may be defined by a short circuit between the wires of two motor winding units. The control unit 120 is also configured to detect such two faulty motor winding units e.g., based on a comparison of the actual electrical current through the motor winding units. In such a fault case, the control unit 120 is configured to determine one of the two faulty motor winding units as the faulty motor winding unit for which the corresponding half bridges DH1 and DL1, DH2 and DL2, or DH3 and DL3 are to be switched off and/or which corresponding half bridges are to be operated with adjusted parameters. Consequently, as discussed above, the electrical motor 51-2 can be further operated by means of the remaining motor units.

In the case of the blood pump for subcutaneous insertion into a heart's ventricle the herein described error tolerant configuration and operation of the motor winding units of the electrical motor driving the blood pump reduces the risk on patients by a total drop out of the blood pump. Further to this the risk imposed by removing the blood pump from the patient for replacing it by a new one be reduced as well.

Finally, the present disclosure proposes a new blood pump for percutaneous insertion and/or intravascular application comprising an electrical motor for driving the blood pump, the electrical motor comprising at least three motor winding units, wherein each motor winding unit is individually connectable to a power supply via two separate phase supply lines connected to the respective motor winding unit terminals.

Further, the present disclosure proposes a motor controller for driving and controlling the electrical motor of the blood pump, wherein the motor controller comprises corresponding phase supply line driving units for each motor winding unit of the electrical motor of the blood pump which phase supply line driving units are connected via the corresponding two-phase supply lines with the corresponding motor winding unit.

Furthermore, the present disclosure proposes a corresponding blood pump system comprising the blood pump and the motor controller.

Moreover, the present disclosure proposes a corresponding control method for controlling the power supply to the motor winding units of the blood pump, wherein the method comprises: detecting a fault of one of the motor winding units, and in case of a detected faulty motor winding unit, switching off the corresponding phase supply line driving units of the faulty motor winding unit and further operating the electrical motor by controlling the phase supply line driving units of the remaining motor windings, or alternatively further operating all motor winding units wherein the driving parameters for the faulty motor winding unit are adjusted driving parameters.

Finally, the present disclosure proposes the use of at least three independent motor windings in an electrical motor for driving of a blood pump for percutaneous insertion and/or intravascular application the blood pump, which motor windings are individually connected to corresponding power supply via corresponding two separate phase supply lines connected to respective motor winding ends of one of the at least three motor windings.

The invention claimed is:

1. A blood pump system for percutaneous insertion comprising:
   a blood pump comprising:
   a pump housing with outlet openings;
   a drive shaft that drives an impeller as a thrust element;
   a catheter comprising a catheter tube through which passes a power supply line;

an electrical motor for driving the blood pump, the electrical motor comprising at least three motor winding units, wherein each motor winding unit is arranged and configured to be individually connected to a power supply via a power supply line comprising separate phase supply lines connected to respective motor winding unit terminals;

a motor controller for driving and controlling the electrical motor of the blood pump, the motor controller comprising corresponding phase supply line driving units for each of the motor winding units which are respectively connected through the corresponding phase supply lines with one of the motor winding units; and a control unit configured to control the phase supply line driving units to operate the electrical motor, wherein the control unit is configured to detect a fault in one of the motor winding units wherein the control unit is further configured, in case of a detected faulty motor winding unit, to adjust driving parameters for the faulty motor winding unit and to further operate the electrical motor by all motor winding units.

2. The blood pump system of claim 1, wherein the motor controller further comprises at least one of:

respective phase current measuring units for measuring an actual value of an electrical current through the corresponding motor winding units;

a total current measuring unit for measuring an actual value of a total electrical current through all of the motor winding units; and respective measuring units configured for measuring a respective induced counter electromagnetic force, CEMF, for the motor winding units not driven.

3. The blood pump system of claim 1, wherein each of the phase supply line driving units is implemented by two corresponding half bridge units configured to be switchable for a cooperative control of electrical power supplied to the corresponding motor winding unit.

4. The blood pump system of claim 1, wherein the control unit is configured to control the phase supply line driving units to operate the electrical motor, to drive and control at least one of a rotational speed of the electrical motor, a rotational direction of the electrical motor, and a torque produced by the electrical motor.

5. The blood pump system of claim 1, wherein the faulty motor winding unit is defined by at least one of an interruption in a wire of the motor winding unit or in the corresponding phase supply lines of the motor winding unit; a current leakage of the motor winding unit to a casing of the electrical motor; and a short circuit between wire turns of the motor winding unit; and wherein the control unit is further configured to detect the faulty motor winding unit based on at least one of the respective actual electrical current through the motor winding units or a comparison of the actual electrical voltage of the motor winding units.

6. The blood pump system of claim 1, wherein the electrical motor is an integral component of the blood pump, which is configured for being completely inserted percutaneously into a patient's body so that when the blood pump is inserted, the motor controller for providing electrical power to and controlling the electrical motor is located outside the patient's body.

7. A blood pump system for percutaneous insertion comprising:

a pump housing with outlet openings;

a drive shaft that drives an impeller as a thrust element;

a catheter comprising a catheter tube through which passes a power supply line;

an electrical motor for driving rotation of an impeller of a blood pump, the electrical motor comprising:

at least three motor winding units, wherein each of the motor winding units is arranged and configured to be individually connected to a power supply via a power supply line comprising separate phase supply lines connected to respective motor winding unit terminals;

a motor controller for driving and controlling an electrical motor of the blood pump system, the motor controller comprising corresponding phase supply line driving units for each of the motor winding units which are respectively connected through the corresponding phase supply lines with one of the motor winding units; and a control unit configured to control the phase supply line driving units to operate the electrical motor, wherein the control unit is configured to detect a fault in one of the motor winding units wherein the control unit is further configured, in case of a detected faulty motor winding unit, to adjust driving parameters for the faulty motor winding unit and to further operate the electrical motor by all motor winding units.

8. The blood pump system of claim 7, wherein the electrical motor is a permanent magnet excited synchronous motor.

9. The blood pump system of claim 7, wherein the electrical motor is an integral component of the blood pump, which is configured for being completely inserted percutaneously into a patient's body so that when the blood pump is inserted, the motor controller for providing electrical power to and controlling the electrical motor is located outside the patient's body.

10. The blood pump system of claim 7, wherein the electrical motor comprises three motor winding units, each motor winding unit being connected to corresponding phase supply lines.

* * * * *